United States Patent [19]
Auersperg

[11] Patent Number: 5,871,941
[45] Date of Patent: Feb. 16, 1999

[54] METHOD OF TESTING EXPRESSION OF CA125 ANTIGEN IN CULTURED OVARIAN SURFACE EPITHELIAL CELLS TO IDENTIFY AND MONITOR INDIVIDUALS HAVING A PREDISPOSITION TO DEVELOP OVARIAN CANCER

[76] Inventor: Nelly Auersperg, 3519 Point Grey Rd., Vancouver, British Columbia, Canada, V6R 1A7

[21] Appl. No.: 508,908

[22] Filed: Jul. 28, 1995

[51] Int. Cl.⁶ .................... G01N 33/574; G01N 33/53
[52] U.S. Cl. .................. 435/7.23; 435/7.21; 436/63; 436/64; 436/813
[58] Field of Search ................. 435/7.23, 7.21; 436/63, 64, 813

[56] References Cited

U.S. PATENT DOCUMENTS

| | | | |
|---|---|---|---|
| 4,921,790 | 5/1990 | O'Brien | 435/7.23 |
| 5,013,547 | 5/1991 | Sweet | 424/85.91 |
| 5,147,783 | 9/1992 | Uda et al. | 435/7.23 |
| 5,320,956 | 6/1994 | Willingham et al. | 435/172.2 |
| 5,366,866 | 11/1994 | Xu et al. | 435/7.23 |

OTHER PUBLICATIONS

Van Niekerk, et al., *Am. J. Pathol.*, vol. 142, No. 1, Jan. 1993.

Scott, *Disease Markers*, vol. 9, pp. 133–152, 1991.

Auersperg, et al., *Am. J. Obstet. Gynecol.*, vol. 173, No. 2, pp. 558–569, Aug., 1995.

P.A. Kruk et al, "A Simplified Method to Culture Human Ovarian Surface Epithelium", Lab. Invest. 1990; 90: 132–136.

N. Auersperg et al, "Human Ovarian Surface Epithelium: Growth Patterns and Differentiation", in Ovarian Cancer III, 1994: 157–169.

*Primary Examiner*—Toni R. Scheiner

[57] ABSTRACT

A screening test for identifying individuals having a predisposition to develop ovarian cancer. The test involves measuring the phenotypic expression of the CA125 antigen in overtly normal ovarian surface epithelium (OSE) cells propagated in vitro. The OSE cells are preferably passaged repeatedly prior to measuring for the expression of the CA125 antigen. The test is based on the finding that OSE cells obtained from individuals having a family history of ovarian and/or breast cancer retain sub-populations of CA125 expressing cells for longer time periods in vitro than OSE cells derived from individuals not having a such a family history. The test provides an alternative means of identifying and monitoring women at risk of developing ovarian cancer, including women with hereditary ovarian cancer syndromes and women likely to develop sporadic (non-familial) ovarian cancer.

10 Claims, 4 Drawing Sheets

METHOD OF TESTING EXPRESSION OF CA125 ANTIGEN IN CULTURED OVARIAN SURFACE EPITHELIAL CELLS TO IDENTIFY AND MONITOR INDIVIDUALS HAVING A PREDISPOSITION TO DEVELOP OVARIAN CANCER

FIELD OF THE INVENTION

This application relates to a screening test for identifying individuals having a predisposition to develop ovarian cancer. The test involves measuring the phenotypic expression of the CA125 antigen in overtly normal ovarian surface epithelium cells propagated in vitro.

BACKGROUND OF THE INVENTION

The effective diagnosis and treatment of cancer at an early stage in its development ordinarily improves the prospects for a successful clinical outcome. Unfortunately, ovarian cancer is notoriously difficult to detect in its early stages.

Over 85% of human ovarian carcinomas are thought to arise from the ovarian surface epithelium (OSE). OSE-derived carcinomas are the fifth or sixth most frequent malignancy in American women and the five year survival rate of patients with ovarian cancer is no better than 37%.

In recent years, the availability of several tumor markers has improved the diagnostic and prognostic accuracy in the management of ovarian carcinomas. Serous cystadenocarcinoma ovarian tumor associated antigen CA125 is currently the serum marker of choice for monitoring the progression of OSE carcinomas. Elevated serum levels of CA125 antigen are detectable in approximately 80–90% of ovarian cancer patients. The presence of CA125 is typically detected by radioimmunoassays employing monoclonal antibodies such as OC125 which bind specifically to the CA125 antigenic determinant.

Various United States patents have previously issued pertaining to the use of monoclonal antibodies to detect the presence of CA125 in sera. For example, U.S. Pat. No. 5,366,866, Xu et al., issued 22 Nov., 1994, relates to a method of diagnosing and monitoring the progression of ovarian and endometrial cancers using monoclonal antibodies reactive with CA125 present in sera, blood plasma or other biological fluids.

While measurement of serum CA125 levels is an effective tool for monitoring the progression of ovarian cancers, it is not reliable as a predictive marker for identifying healthy women at increased risk for ovarian cancer, or for detection of very early stages of the disease. Some women who are at an increased risk to develop ovarian cancer can be identified on the basis of family histories of ovarian, breast, or other related cancers and by genetic analysis. Numerous cytogenetic studies and loss of heterozygosity investigations have begun to suggest some genes or chromosomal regions involved in ovarian cancer initiation and progression (Pejovic et al., Genes Chromosomes Cancer, 1992; 4:58–68; Testa et al., Cancer Res., 1994; 54:2778–2784; Yang-Feng et al., Int. J. Cancer, 1993; 54:546–551). In situations where linkage analysis is feasible and linkage of affected family members can be shown through the only currently known locus, BRCA-1, family members predisposed to develop ovarian and/or breast cancer can be identified with good accuracy (Futreal et al., Science, 1994; 266:120–122). There are, however, individuals in families that may be linked through some yet to be identified locus or where linkage testing is not feasible. Such individuals could benefit from an alternative identification-of-risk strategy. Not all women in currently recognized risk categories will develop ovarian cancers, and additional contributing factors are poorly defined. The majority of ovarian cancers arise "sporadically" (i.e. in women without family histories).

One alternative strategy is to identify preneoplastic phenotypic changes in the OSE which could signal a predisposition to development of ovarian tumors. Unfortunately, little progress has been made thus far in the early detection of such preneoplastic tissue changes and no reliable tumor-associated tissue markers have yet been identified. This lack of information about early changes in the OSE poses a particular problem for women with hereditary ovarian cancer syndromes, where there is a need to define more reliable criteria for prevention and surveillance.

The need has therefore arisen for a new screening test for identifying and monitoring women at risk of developing OSE-derived carcinomas.

SUMMARY OF THE INVENTION

A method of testing an individual to identify a predisposition to develop ovarian carcinomas is disclosed. The method includes the steps of (a) obtaining a sample of overtly normal ovarian surface epithelial (OSE) cells from the individual; (b) culturing the OSE cells in vitro to obtain a population of propagated OSE cells derived from the sample; and (c) measuring the expression of CA125 antigen by the propagated OSE cells.

The sample may be derived from a site of overtly normal ovarian surface epithelium wherein the CA125 antigen is not consistently expressed in vivo. Preferably the propagated OSE cells are repeatedly passaged in vitro prior to the measuring step. CA125 antigen expression is measured by reacting the propagated OSE cells with an antibody having a high specificity against CA125 and determining the proportion the OSE cells having antibody-antigen complex present. OC125 is a suitable monoclonal antibody to use for this purpose.

The method may further include the step of determining the proportion of the propagated OSE cells which maintain a typical epithelial morphology in each passage.

The sample is preferably obtained by scraping the OSE cells from an outer surface of an ovary of the individual. This procedure may be carried out using a laparoscope or by means of more invasive surgical procedures.

BRIEF DESCRIPTION OF THE DRAWINGS

In drawings which illustrate the preferred embodiment of the invention, but which should not be construed as restricting the spirit or scope of the invention in any way, FIG. 1 is a graph illustrating the results of experiments measuring the proportion of ovarian surface epithelial cells which express the CA125 antigen relative to the number of passages in culture. The left column relates to tissue obtained from women with no family history (NFH) of ovarian cancer; the middle column relates to tissue obtained from women with a minor family history (mFH) of ovarian cancer; and the right column relates to women with a strong family history (FH) of ovarian cancer. The symbol ◑ denotes women who themselves had borderline or malignant ovarian neoplasms in the contralateral ovary. Four FH cases that were linkage positive for BRCA-1 are indicated by asterisks. Cultures derived from the right and left ovaries of the same patient are denoted by identical letters beside the symbols. For cultures from the same ovary that were examined in more than one passage, the symbols are connected by lines.

FIGS. 2A-1–2A-3 are a series of bar graphs illustrating the predominant morphology of ovarian surface epithelium at different passages in culture. FIG. 2A-1 relates to culture of tissue obtained from women with no family history (NFH) of ovarian cancer; FIG. 2A-2 relates to culture of tissue obtained from women with a minor family history (mFH) of ovarian cancer; and FIG. 2A-3 relates to culture of tissue obtained from women with a strong family history (FH) of ovarian cancer. The symbol ☐ denotes compact epithelial cells; ▨ denotes flat epithelial cells; and ■ denotes atypical cells. The numbers above the bars denote the percentage of cultures having the corresponding morphology.

FIGS. 2B-1–2B-3 are a series of bar graphs illustrating the results of experiments measuring the proportion of ovarian surface epithelial cultures which express the CA125 antigen relative to the number of passages in culture and cellular morphology. FIG. 2B-1 relates to culture of tissue obtained from women with no family history (NFH) of ovarian cancer; FIG. 2B-2 relates to culture of tissue obtained from women with a minor family history (mFH) of ovarian cancer; and FIG. 2B-3 relates to culture of tissue obtained from women with a strong family history (FH) of ovarian cancer. The symbol ☐ denotes compact epithelial cells; ▨ denotes flat epithelial cells; and ■ denotes atypical cells. The numbers above the bars denote the percentage of CA125 positive cells in the corresponding cultures.

DETAILED DESCRIPTION OF THE PREFERRED EMBODIMENT

1.0 INTRODUCTION

The ovarian surface epithelium (OSE) is the modified pelvic mesothelium that covers the ovary. It comprises only a minute fraction of the total ovarian mass but it is thought to be the source of most human ovarian carcinomas, including those varieties which contribute most to cancer mortality. At present there are no reliable means of early detection or prevention of OSE-derived carcinomas. As a result, ovarian cancers are frequently incurable when first diagnosed.

In spite of its clinical importance, no suitable animals models for the in vivo investigation of OSE tissue exist. In most animal species ovarian carcinomas tend not to arise in the OSE and hence animal studies cannot be reliably extrapolated to human beings.

Fortunately, improved techniques for isolating, propagating, and characterizing human OSE cells in culture have recently been developed (Kruk et al., Lab Invest., 1990; 90:132–136). This has enabled in depth tissue studies of OSE physiology and pathology.

Women with a strong family history of ovarian cancer, and especially those who are obligate gene carriers based on linkage analysis, have a greatly increased probability of developing ovarian carcinomas at a relatively young age (Lynch et al., Cancer, 1993; 71:573–581). Histologic studies of ovarian tissue from women with a family history of ovarian cancer, and of the contralateral normal ovary of individuals with unilateral ovarian cancer, have revealed benign changes in the OSE and stroma (Resta et al., Obstet. Gynecol., 1993; 82:181–186; Mittal et al, Int. J. Gynecol. Pathol., 1993; 12:59–63). To test the hypothesis that overtly normal OSE from healthy women having a predisposition to develop ovarian cancer might express phenotypic differences that could be exploited as predictive markers, the applicant analyzed OSE cultures from women with and without such family histories for the expression of a known ovarian cancer marker, namely the CA125 antigen. The expression of this antigen was investigated in relation to passages (cell doublings) in culture, cell morphology and cell density.

CA125 is a mucin-like antigenic determinant that was originally derived from an ovarian serous cystadenocarcinoma. It is secreted predominantly by non-mucinous common epithelial tumors of the ovary and is widely used in serum tests to monitor the progression and management of ovarian cancers (Yedema et al., Br. J. Cancer, 1993; 67:1361–1367). However, serum levels of CA125 are not usually elevated in women prior to development of ovarian tumors, or at very early stages of the disease.

In adult women, CA125 is normally present in extraovarian mesothelial cells but it is notably absent or inconsistently present in the OSE in vivo (Jacobs et al., Hum. Reprod., 1989; 4:1–12; Nouwen et al., Am. J. Pathol., 1987; 126:230–242; Kabawat et al., Int. J. Gynecol. Pathol. 1983; 2:275–285). In humans and other mammalian species, CA125 is also found in the oviductal and uterine epithelia, in respiratory epithelium, amniotic fluid, milk and cervical mucus. Because of its tissue-specific distribution, CA125 has been defined as a differentiation antigen (Jacobs et al., supra; Nouwen et al., Differentiation, 1990; 45:192–198).

While CA125 staining of normal OSE on the ovarian surface is often weak or absent, the OSE in inclusion cysts and the bottoms of crypts is more consistently CA125 positive. The OSE lining these regions tends to assume the characteristics of epithelia of Mullerian duct origin, and the expression of CA125 is likely part of this phenotypic modulation. At the same time, inclusion cysts and crypts have been proposed as preferred sites of early (pre) neoplastic changes. It would seem, therefore, that changes in CA125 expression may occur very early, or even precede, neoplastic progression in OSE cells which are situated in sites that are particularly prone to malignant transformation, and perhaps also in cells from individuals with a high probability to develop ovarian cancer.

The applicant has determined that when overtly normal OSE cells obtained from individuals having a family history of ovarian and/or breast cancer and cells obtained from individuals with no such family history are propagated in culture, there is marked difference in the pattern of CA125 expression. As used in this specification, the term "overtly normal" refers to OSE cells obtained from grossly normal ovaries which are of normal epithelial morphology and which do not exhibit any characteristics of malignant transformation.

2.0 EXAMPLE

The present invention is described in further detail in the following Example which is illustrative and should not be taken as restricting the scope of the inven- tion in any way.

2.1 Experimental Materials and Methods (a) Source of cells.

Ovarian specimens were obtained from 18 women with no family history of breast/ovarian cancer (NFH). In addition, 5 women were included in the study who had a minor family history (mFH), i.e. first or second degree relatives with cancer of the ovary, breast and/or colon, but whose pedigree did not convincingly demonstrate a familial or hereditary basis for these neoplasms. Particulars of the mFH cases are set forth in Table 1 below.

TABLE 1

Patients with a minor family history (mFH)* of ovarian, breast or colon cancer

| Case | 1st degree relatives | | | 2nd degree relatives | | |
|---|---|---|---|---|---|---|
| | Ovary | Breast | Colon | Ovary | Breast | Colon |
| OSE-29 | | | | 1 | | 1 |
| OSE-51 | | 1 | | | | |
| OSE-53 | 1 (ovary or colon)† | | | 1 | 1 | 1 |
| OSE-57 | | | 1 | | | 2 |
| OSE-70 | 1 | | | | | |

*defined as a family history that does not include two or more first-degree relatives with cancer of the ovary or breast.
†abdominal carcinomatosis, primary unknown. All malignancies in this patient's family were on the maternal side.

Seven women studied had strong family histories (FH), as defined by at least two first degree relatives with ovarian and/or breast cancer. Within this group, four patients were found to be linkage positive to the BRCA-1 locus, and these individuals underwent prophylactic oophorectomies. All other tissue specimens were obtained from grossly normal ovaries at the time of surgery for nonmalignant gynecologic diseases. Histopathologic analysis confirmed the absence of ovarian neoplasms in all specimens. However, two members of the NFH group and one in the FH group had a history of concurrent or previous ovarian neoplasms (borderline or malignant) in the contralateral ovary.

(b) Cell culture.

OSE cells were scraped from the ovarian surface and cultured as described previously in "A simplified Method to Culture Human Ovarian Surface Epithelium", P. A. Kruk et al., Lab Invest. 1990; 90:132 at pages 132–134 which is hereby incorporated by reference. The scrape method takes advantage of the tenuous attachment of OSE to underlying tissue and generates epithelial fragments which produce monolayers in culture, with little contamination from other cell types. The scrape method is superior to the explant method in terms of speed, simplicity, higher purity of cultures and increased cell yield. Cells may be harvested using the scrape method in a minimally invasive manner using a laparoscope.

Culture reagents were obtained from GIBCO (Grand Island, N.Y.) and Sigma (St. Louis, Mo.) and serum was from Hyclone (Logan, Utah). The specimens were collected aseptically and were cultured in Sigma medium 199:MCDB-105/15% fetal bovine serum (FBS) with 25 ug/ml gentamicin. In 5 of the 7 familial cases, the OSE from the right and left ovaries were studied separately, thus providing a total of 12 independently grown cultures. The cells' origin as OSE was initially confirmed by their characteristic epithelial morphology and keratin expression.

Cultured cells were passaged with 0.06% trypsin (1:250) and 0.01% EDTA when confluent. To attain confluence, the cells underwent 3–4 population doublings in primary culture, and approximately 3 population doublings in each further passage. NFH and mFH cultures were analyzed in primary culture and in passages 1–4, while the FH cultures were available for analysis in passages 2–4.

Cultures from three NFH patients, one mFH patient and eight FH patients were immortalized by transfection with Simian Virus 40 (SV40) early genes in passages 1–5, using either the calcium phosphate method or lipofectin (GIBCO). In three of the FH cases, cells obtained from the right and left ovaries were immortalized separately, resulting in eleven immortalized lines.

(c) Assays.

The expression of CA125 by cultured OSE cells was demonstrated immunocytochemically and by radioimmunoassay (RIA). For immunocytochemistry, cultured cells and paraffin embedded sections of ovaries were fixed in 10% buffered formalin for 15 minutes and rinsed in PBS. Endogenous peroxidases were blocked with 0.6% $H_2O_2$ in MeOH, and the cultures brought through graded alcohols to PBS. Samples were pre-incubated in 5% normal goat serum followed by a 1 hour incubation with Mab OC125 diluted 1:1000 for ovary sections and 1:2000 for cultured cells. Then, HRP-labelled goat-anti-mouse IgG was added for 1 hour. Color was developed in 0.025% DAB /.01% $H_2O_2$/ 0.04% $NiCl_2$. The ovarian carcinoma line OVCAR-3 was used as the positive control, and development time adjusted for the optimal intensity of its reaction. Omission of the primary antibody, as well as human dermal fibroblasts served as negative controls. The number of CA125 positive cells was counted and percentages calculated based on at least 600 cells. If the proportion of stained cells appeared to vary from one part of the coverslip to another, then up to 1200 cells were counted to assure representative results. The counts were based on the cells present within random microscopic fields, in regions of the cultures where the cells were neither extremely crowded nor extremely sparse, to avoid variations based on cell density. Radioimmunoassays for CA125 were carried out on culture media that had been conditioned by the cells for 7 days. The media were centrifuged to remove cell debris, and frozen at −70° C. until the time of assay. Some samples were concentrated using Amicon Centricon 30 microconcentrators. All samples were assayed using the Abbott CA125 kit according to the manufacturer's directions. Values below 15 U/ml were considered too close to the baseline and thus negative.

2.2 Expression of CA125 antigen

CA125 expression in histologic sections of NFH and mFH biopsy specimens was low and inconsistent in the surface OSE, but relatively common on papillae, in invaginations, and in metaplastic cells independently of location. This histologic variation correlated fairly consistently with the proportion of OSE cells that stained immunohistochemically for CA125 in primary culture. Among 15 primary and passage 1 NFH and mFH cultures, CA125 at levels of >15 IU/ml was detected by RIA in the medium of the 4 cultures with the highest percentage of CA125 positive cells. Histologic sections of the FH cases were not available.

Figure 1:
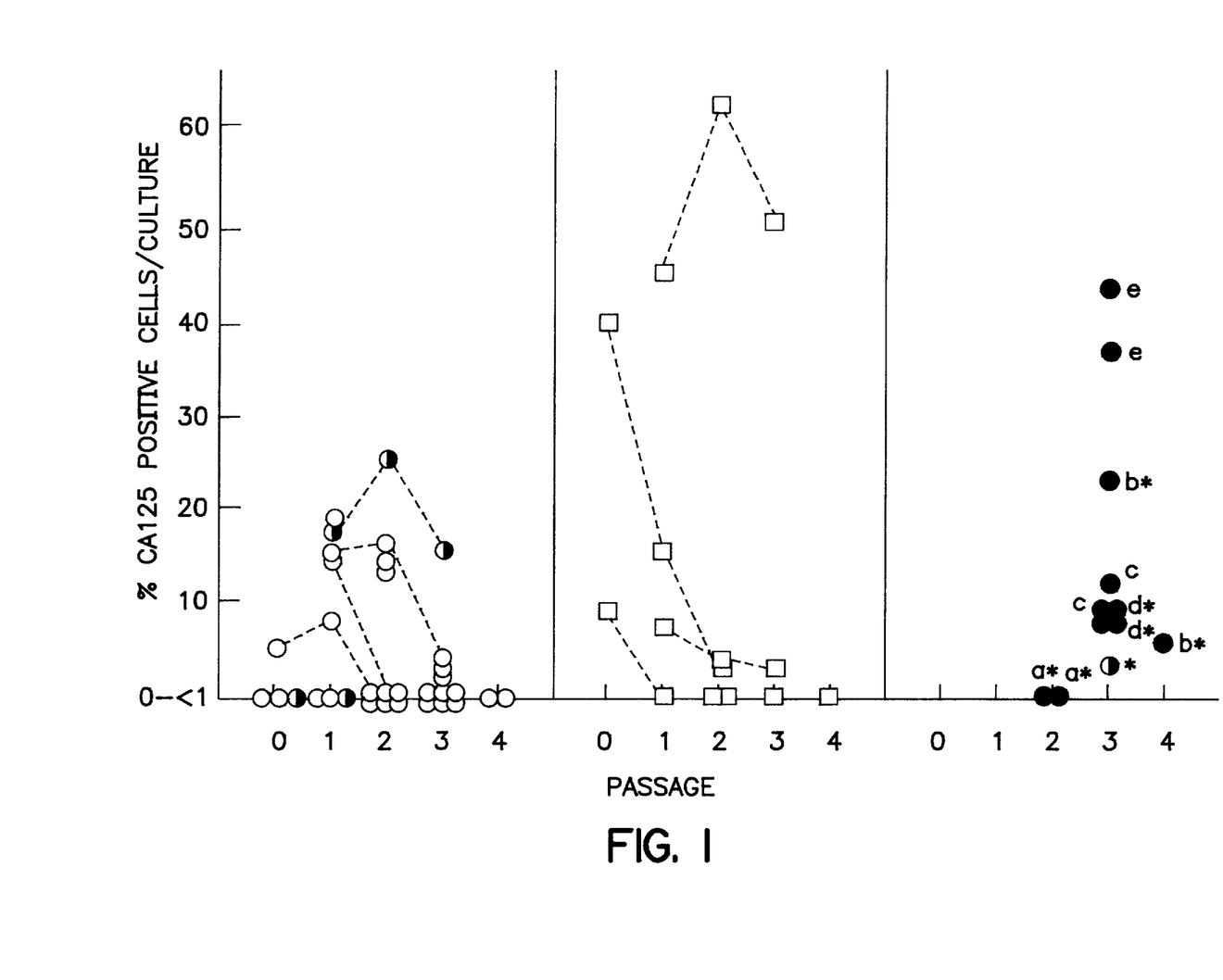

FIG. 1 shows the changes in the proportions of CA125 positive cells with passages and family history (see Brief Description of Drawings above for an explanation of special symbols). Of four NFH cases examined in primary culture, three cultures had less than 1% CA125 positive cells, and in one culture (25% of cases) 5% of cells were CA125 positive. Upon subsequent passage, the proportion of cultures with 5% or more CA125 positive cells increased to 58% in passage 1, was 30% in passage 2, and 8% in passages 3 and 4. Thus, as shown in FIG. 1, CA125 production in NFH cultures diminished rapidly after passage 1.

Compared to the NFH cases, cultures derived from mFH patients included some with exceptionally high proportions of CA125 positive cells. However, CA125 expression again diminished with passages and, with one exception, all mFH cultures contained less than 5% positive cells in passages 2 to 4 (FIG. 1).

The FH cases showed a markedly different pattern of CA125 expression in culture. As illustrated graphically in FIG. 1, five percent or more of the cells were CA125 positive in 9 of 12 (82%) cultures in passages 2–4, and in 9 of 10 (90%) cultures in passages 3–4. Thus, FH cultures retained subpopulations of CA125-expressing cells over longer time periods and more population doublings than did either NFH cultures or mFH cultures under identical conditions. In other words, CA125-expressing cells tend to disappear with passaging in women without, but not in women with, a familial predisposition to develop ovarian cancer.

CA125 expression in the cultures of four known BRCA-1 linkage positive patients varied: one case, tested in passage 2, had less than 1% CA125 positive cells. In three cases tested in passages 3–4, the percentage of positive cells ranged from 3% to 22%. There was good agreement in the proportions of CA125 expressing cells when FH cultures from the two ovaries of individual patients were grown independently and compared.

In four of the cases discussed above, special features should be noted. One mFH case, OSE-53, exhibited the largest proportion of CA125 positive cells in the whole study (45–62%), and this phenotype persisted with passage, as in FH cultures. In addition to a suggestive family history, histologic examination showed that the OSE in this patient's ovarian biopsy specimen was columnar, ciliated and intensely CA125 positive not only in inclusion cysts but also on the ovarian surface. Three women had histories of ovarian neoplasms, and they are identified by the special symbol ◑ in FIG. 1. In one of these, an NFH case, a lesion diagnosed as "cystadenoma, possible borderline low malignancy adenocarcinoma" was found in the contralateral ovary at the time of the surgery. CA125 expression of this patient's OSE cells was still high when last tested in passage 3, similar to the FH cultures. In contrast, a second NFH patient had a mucinous ovarian adenocarcinoma, stage II-c, grade I, removed two years previously. The cultures from the remaining ovary were morphologically atypical and CA125 negative, i.e. characteristic of NFH when tested in primary culture and passage 1. One FH patient, who was also BRCA-1 linkage positive, had a unilateral ovarian cancer at the time of surgery. The OSE from the other ovary produced cultures that were epithelial and 3% CA125 positive in passage 3 (FIG. 1).

All immortal lines were completely CA125 negative although one of them (OSE-53) was transfected with SV40 when 39% of cells were CA125 positive. In the carcinoma lines OVCAR 3 and CaOV3, varying proportions of cells were CA125 positive. A striking difference between the carcinoma lines and OSE was the presence of mitotic cells that expressed the antigen.

2.3 Morphology and cellular antigen distribution

FIGS. 2A-1–2A-3 are a series of bar graphs illustrating the predominant morphology of ovarian surface epithelium at different passages in culture from women without a family history (NFH), with a minor family history (mFH), and a strong family history (FH) of ovarian cancer. FIGS. 2A-1–2B-3 are a series of bar graphs correlating the expression of CA125 antigen to cellular morphology and number of passages in culture.

Figure 2A:
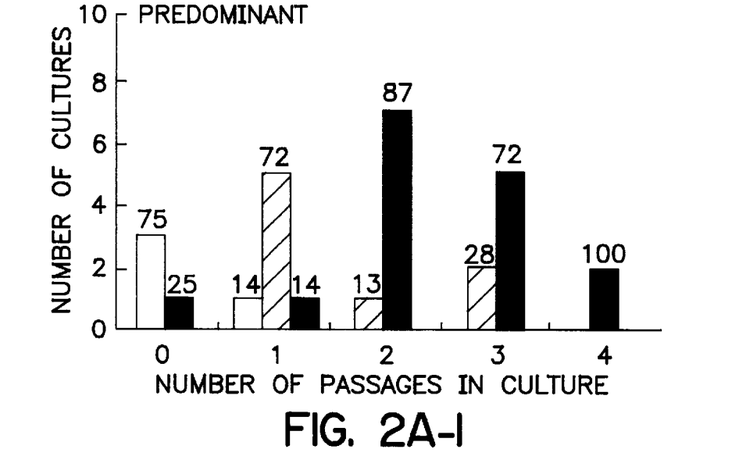
Figure 2A:
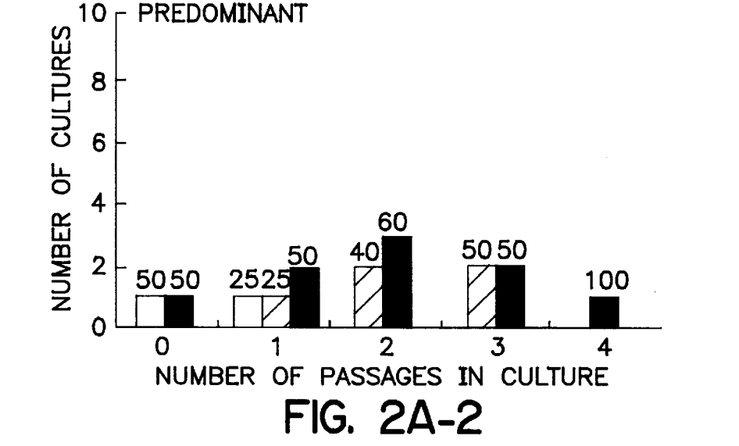
Figure 2A:
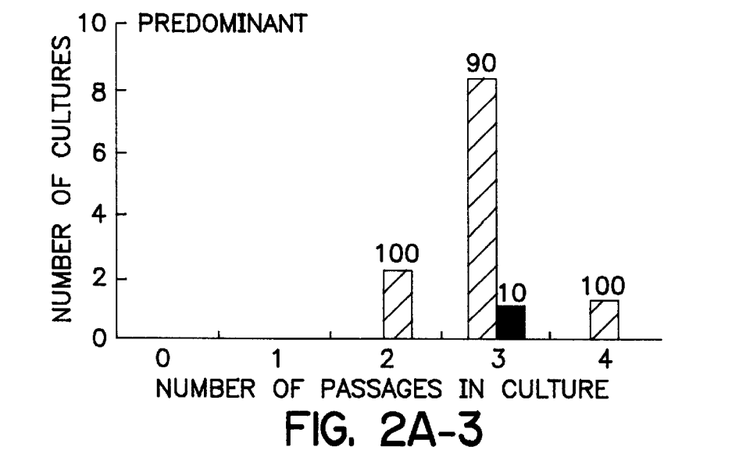

As shown in FIG. 2A-1, NFH-OSE formed predominantly compact, cobblestone epithelial monolayers in primary cultures. Most cells modulated to a flat epithelial form by passage 1 and, after 2–4 passages, to an atypical form and a growth pattern which is reminiscent of but not identical to fibroblasts. In contrast to the NFH cultures, almost all FH cultures shown in FIG. 2A-3 retained a flat epithelial phenotype throughout the experimental study. The morphologic changes among the mFH cultures shown in FIG. 2A-2 were intermediate between the other two groups.

Figure 2B:
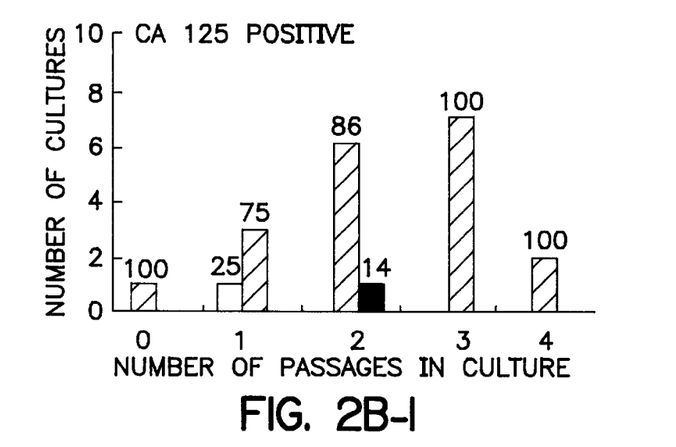
Figure 2B:
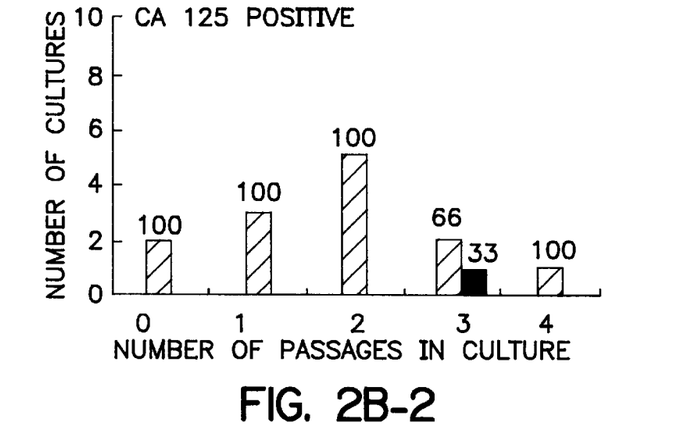
Figure 2B:
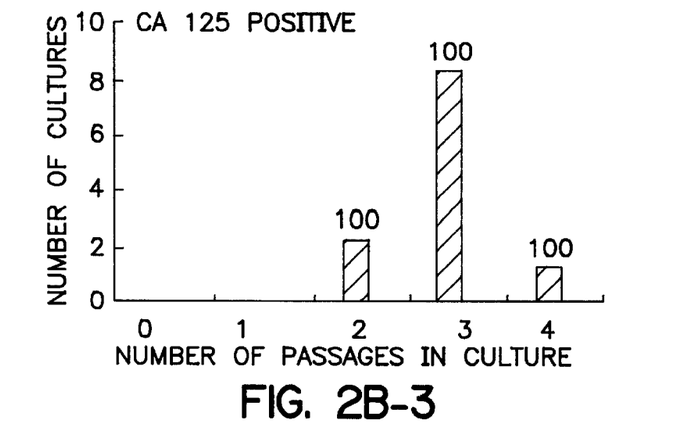

The subcellular distribution of CA125 varied with the cell cycle, cell shapes and cell density, and was similar in FH, mFH and NFH cultures. CA125 staining increased with cell density, was consistently absent in mitotic cells and rapidly growing populations, and was usually absent in atypical and senescent cells. Staining tended to be faint and intracellular in the small, compact epithelial cells characteristic of primary cultures, but became intense when OSE assumed the flat epithelial morphology which often followed their first subculture. As shown graphically in FIGS. 2B-1–2B-3, CA125 positive cells were almost exclusively of the large, flat epithelial type.

Figure 3A:
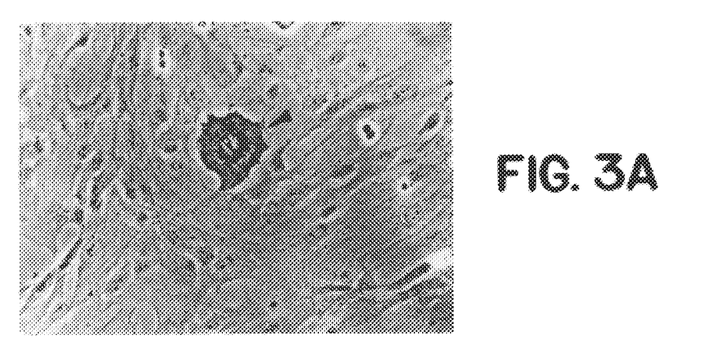
FIG. 3(a) is a photomicrograph (180X) of an ovarian surface epithelial cell culture derived from a NFH subject at passage 3 stained immunohistochemically for CA125.
Figure 3B:
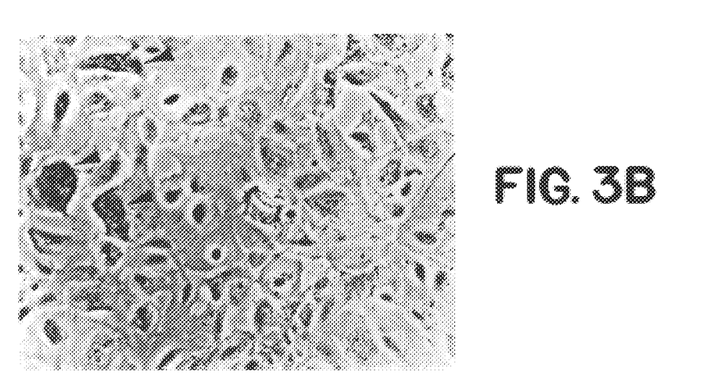
FIG. 3(b) is a photomicrograph (180X) of an ovarian surface epithelial cell culture derived from a FH subject at passage 3 stained immunohistochemically for CA125.

FIG. 3A relates to a NFH culture at passage 3. The predominant morphology is atypical (fibroblast-like), but the one CA125 positive cell in the field is flat, epithelial. FIG. 3B shows a FH culture at passage 3. The predominant morphology, by contrast, is flat, epithelial and arrowheads point to several CA125 positive cells.

3.0 DISCUSSION

The applicant has determined from the above studies that overtly normal OSE from women with family histories (FH) of ovarian cancer appear to differ from the OSE of women with no family histories (NFH) not only at the genetic level, but also phenotypically. The observed differences between NFH-OSE and FH-OSE phenotypes may not be detectable in the intact epithelium. Rather, the differences between the NFH and FH cases only clearly emerge when the cells are propagated in culture. It appears that NFH-OSE and FH-OSE cells respond differently to a particular set of environmental signals encountered upon explantation into culture: NFH-OSE cells respond to the culture environment by modulation to a more mesenchymal phenotype which includes a fibroblast-like shape, reduced intercellular adhesion, the ability to contract collagen gels, the expression of stromal extracellular matrix components, loss of epithelial markers such as keratin and desmoplakin, and, most importantly, loss of the CA125 epithelial marker. As indicated above, CA125 expression disappeared within a few passages in NFH-OSE cultures. In contrast, a high proportion of FH-OSE cells retained their epithelial morphology and continued to produce CA125 in late passages.

It has been known for a long time that cells, in general, respond to explantation into culture as they would to wounding, and that they consequently undergo changes in phenotype and in gene expression that are seen in regenerative responses and wound healing. Specific signals that elicit this response include the disruption of intercellular contacts and the exposure to serum which, in vivo, cells encounter only at sites of tissue damage. By analogy, the response of NFH-OSE to explantation into culture mimics the response that occurs in vivo during post-ovulatory repair, where OSE cells disperse, migrate, proliferate and modulate to a more fibroblast-like shape. The reduced conversion to a stromal phenotype by the FH-OSE cells, as observed in the experiments described above, suggests that the epithelial phenotype of FH-OSE is more stable and less responsive to the environmental signals that are encountered in culture. Such loss of responsiveness, or increased autonomy, is one of the hallmarks of neoplastic progression.

As discussed above, the CA125 ovarian tumor marker is a mucin epitope which, in the intact ovary, occurs only sporadically in normal OSE but is expressed more strongly and consistently in inclusion cysts and in benign and malignant ovarian neoplasms (Jacobs et al., supra; Shaw et al., Tumor Biol., 1988;9:101–109). The applicant has determined that immortalization of OSE cells with SV40 correlates with a decline in CA125 expression. It may be significant that immortalization by SV40 interferes with the functions of the tumor suppressor genes p53 and RB, and that alterations in p53 appear to play a major role in ovarian cancer. The pattern of CA125 expression observed by the applicant, and the finding that such expression is lost upon immortalization, is consistent with the suggestion that CA125 is an epithelial differentiation antigen (Jacobs et al., supra; Nouwen et al., Differentiation, 1990;45:192–198).

There may be a developmental explanation for the applicant's findings. As indicated above, in the adult woman, OSE is largely CA125 negative while the Mullerian epithelia and the extraovarian mesothelia are CA125 positive. This difference exists as early as in the first trimester fetus. Kabawat et al. (Int. J. Gynecol. Pathol., 1983; 2:275–285) have suggested that the localized lack of CA125 in adult OSE might reflect the acquisition, during development, of properties that are distinct from those of the other derivatives of coelomic epithelium, and that this divergence in differentiation could occur either before or after CA125 is expressed by the Mullerian ducts and extraovarian mesothelium. However, it is also possible that OSE does not undergo the developmental step(s) that lead to CA125 expression in the other sites but, rather, remains competent but not committed to differentiation into a CA125 positive epithelium. The latter hypothesis suggests that OSE may be more primitive and closer to a stem cell form than the other coelomic epithelial derivatives, and could account for the striking capacity of OSE to change phenotypes in response to physiological and pathological influences. This capacity includes the unusual tendency of ovarian carcinomas, which arise in an epithelium that is relatively simple structurally and functionally, to become more highly differentiated with tumor progression as the neoplastic cells acquire the complex epithelial characteristics of Mullerian duct derivatives.

The concept of OSE as a primitive epithelium of mesodermal origin is also in keeping with the coexpression of epithelial and stromal characteristics by adult OSE in vivo and in culture (Czernobilsky et al., Europ. J. Cell. Biol., 1985; 37:175–190; Auersperg et al., Lab Invest., 1994; 71:510–518). This expression of stromal characteristics is reduced in ovarian carcinomas (Dyck et al., Proc. Am. Assn. Cancer Res. 1994; 35:162). Thus, with neoplastic progression, OSE cells become more firmly committed to an epithelial phenotype. The increased stability of the epithelial phenotype observed in the FH-OSE might be related to the increased propensity of these cells to undergo neoplastic transformation. It should also be noted that a small but significant proportion of women, who undergo prophylactic oophorectomies because of high familial cancer risk, subsequently develop cystadenocarcinomas which appear to arise in the extraovarian mesothelium but resemble ovarian cancers histologically (Lynch et al., Am. J. Med. 1986; 81:1073–1076). Such a familial peritoneal ovarian carcinomatosis syndrome could reflect a generalized defect in the maturation of the patient's pelvic mesothelial cells (Tobacman et al., Lancet 1982; 2:795–797).

In summary, the applicant has identified a relationship between the expression of the CA125 phenotype in OSE cells propagated in culture and susceptibility to ovarian cancer. The applicant's findings, in combination with the distinct histologic phenotype of ovaries with a high probability to develop malignant tumors, suggest that the predisposition of OSE from some individuals to undergo malignant transformation is at least in part a dominant process. This is in contrast to a process initially driven by inactivation of both alleles of a gene as would be considered to occur in a process driven by a classical tumor suppressor gene.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of testing an individual to identify a predisposition to develop ovarian carcinomas, said method comprising the steps of:
   (a) obtaining a sample of overtly normal ovarian surface epithelial (OSE) cells from said individual;
   (b) culturing said OSE cells in vitro to obtain a population of propagated OSE cells derived from said sample; and
   (c) measuring the expression of CA125 antigen by said propagated OSE cells.

2. The method of claim 1, wherein said propagated OSE cells are repeatedly passaged in vitro prior to said measuring step.

3. The method of claim 2, wherein said sample is derived from a site of overtly normal ovarian surface epithelium wherein said CA125 antigen is not consistently expressed in vivo.

4. The method of claim 3, wherein said measuring step comprises reacting said propagated OSE cells with an antibody having a high specificity against CA125 antigen and determining the proportion said OSE cells having antibody-antigen complex present.

5. The method of claim 4, wherein said antibody is OC125 monoclonal antibody.

6. The method of claim 5, further comprising the step of determining the proportion of said propagated OSE cells which maintain a typical epithelial morphology in each passage.

7. The method of claim 1, wherein said sample is obtained by scraping said cells from an outer surface of an ovary of said individual.

8. The method of claim 1, wherein said sample is obtained from said individual prior to the onset of histopathologic changes indicative of ovarian carcinogenesis.

9. A method of identifying and monitoring individuals having a predisposition to develop ovarian carcinomas, said method comprising the steps of:
   (a) obtaining a sample of overtly normal ovarian surface epithelial (OSE) cells from a human subject;
   (b) culturing said sample of OSE cells in vitro to obtain a population of propagated cells derived from said sample;
   (c) measuring the expression of CA125 antigen by reacting some of said propagated cells with an antibody having a high specificity against CA125 antigen and determining the proportion of said OSE cells having antibody-antigen complex present; and
   (d) repeating the measuring step recited in sub-paragraph (c) at different time intervals.

10. The method of claim 9, wherein said time intervals are spaced approximately three to seven days apart.

* * * * *

UNITED STATES PATENT AND TRADEMARK OFFICE
CERTIFICATE OF CORRECTION

PATENT NO. : 5,871,941
DATED : February 16, 1999
INVENTOR(S) : Nelly Auersperg

It is certified that error appears in the above-indentified patent and that said Letters Patent is hereby corrected as shown below:

On the title page, , add:

[73] Assignee: The University of British Columbia
Vancouver, Canada

Attorney, Agent, or Firm - Oyen Wiggs Green & Mutala

Signed and Sealed this

Twentieth Day of July, 1999

Attest:

Attesting Officer

Q. TODD DICKINSON

Acting Commissioner of Patents and Trademarks